(12) United States Patent
Fischer

(10) Patent No.: US 8,954,173 B1
(45) Date of Patent: Feb. 10, 2015

(54) METHOD AND APPARATUS FOR PROFILING AND IDENTIFYING THE SOURCE OF A SIGNAL

(76) Inventor: Mark Fischer, Rio Vista, CA (US)

(*) Notice: Subject to any disclaimer, the term of this patent is extended or adjusted under 35 U.S.C. 154(b) by 1509 days.

(21) Appl. No.: 12/203,739

(22) Filed: Sep. 3, 2008

(51) Int. Cl.

| | |
|---|---|
| G06F 17/00 | (2006.01) |
| G01V 1/00 | (2006.01) |
| G06F 17/15 | (2006.01) |
| G06G 7/12 | (2006.01) |
| G06K 9/00 | (2006.01) |
| G10L 17/26 | (2013.01) |
| G06F 17/14 | (2006.01) |
| A01K 29/00 | (2006.01) |

(52) U.S. Cl.
CPC .......... *G06K 9/00516* (2013.01); *G10L 17/26* (2013.01); *G06F 17/148* (2013.01); *A01K 29/005* (2013.01)
USPC .................. 700/94; 367/42; 708/5; 708/815; 708/424

(58) Field of Classification Search
CPC .. G10L 17/26; A01K 29/005; G06K 9/00516; G06K 9/00536; G06F 17/05; G06F 17/148
USPC .................. 700/94; 367/38, 40, 42; 382/278; 708/813, 814, 815, 422, 424, 400, 5
See application file for complete search history.

(56) References Cited

U.S. PATENT DOCUMENTS

| | | | | |
|---|---|---|---|---|
| 6,038,579 | A * | 3/2000 | Sekine .......................... | 708/400 |
| 8,226,568 | B2 * | 7/2012 | Watson et al. ................ | 600/502 |
| 2001/0044719 | A1 * | 11/2001 | Casey ............................ | 704/245 |
| 2003/0125946 | A1 * | 7/2003 | Hsu ................................ | 704/246 |
| 2005/0049877 | A1 * | 3/2005 | Agranat ......................... | 704/270 |
| 2006/0233390 | A1 * | 10/2006 | Causevic et al. ............. | 381/94.1 |
| 2010/0114813 | A1 * | 5/2010 | Zalay et al. ................... | 708/400 |

OTHER PUBLICATIONS

Peng, et al. "Applicaiton of the wavelet transform in machine condition monitoring and fault diagnostics: a review with bibliography", 2004, Mechanical Systems and Signal Processing 18, pp. 199-221.*

* cited by examiner

*Primary Examiner* — Jesse Elbin
(74) *Attorney, Agent, or Firm* — DLA Piper LLP (US)

(57) ABSTRACT

A method and apparatus for profiling and identifying the source of a signal is provided. A first method includes receiving a signal produced by a known source and creating a matrix of wavelet coefficients corresponding to a wavelet transform of the signal. The method also includes profiling the signal according to an output of a wavelet transform utilizing a particular base function and a particular scale set. A second method includes performing a wavelet transform having a particular profile on a received signal and determining the presence of a particular signal-producing entity as a function of wavelet coefficients exceeding a threshold. An apparatus includes a receiver configured to receive a signal and a processor coupled to the receiver, such that the processor is configured to perform wavelet transforms on the signals. A database is coupled to the processor and configured to store wavelet transform profiles.

14 Claims, 7 Drawing Sheets

METHOD AND APPARATUS FOR PROFILING AND IDENTIFYING THE SOURCE OF A SIGNAL

TECHNICAL FIELD OF THE INVENTION

The present invention is directed towards profiling and identifying the source of a signal. More specifically, the present invention is directed towards efficiently identifying the source of a signal by utilizing wavelet transforms to profile a signal produced by a known source, so as to create a filter for identifying the source via the wavelet transform profile.

BACKGROUND OF THE INVENTION

It is often the case in a variety of studies of wild animals that their presence can be known by sound alone. This occurs, for example, with insects and birds whose visibility is often obscured by plant life. Another common case is with the study of cetaceans. Many species are visible at the surface for only minutes at a time, and then only under ideal sea conditions.

It is conceivable that under ideal conditions (e.g., a good source and a tuned system as described later) an individual source could be recognized by sound alone. For example, spectrum analysis via the use of Fourier Transforms could be used. Fourier transforms use the sinusoidal as a basis, wherein the purpose of performing a Fourier transform is to calculate the coefficients of a series of sinusoidal waves of different frequencies, the sum of which are a close approximation of the original signal. By knowing these coefficients one can gain an understanding of the distribution of the signal in question in what is known as "frequency space" or the "frequency domain."

The use of Fourier analysis, however, has many limitations. For example, Fourier analysis yields a high rate of false positives and is significantly affected by noise at or near the same frequencies as the desired feature. Fourier analysis is also computationally inefficient since it utilizes a substantial amount of processing power. Accordingly, it is desirable to provide a method and apparatus for characterizing the acoustics of a particular species in order to design a system that can provide more efficient and reliable detection performance.

SUMMARY OF THE INVENTION

In an embodiment of the present invention, a method for profiling a signal-producing entity is provided. The method includes receiving a signal produced by a known source and creating a matrix having a plurality of wavelet coefficients. Within such embodiment, each of the wavelet coefficients correspond to an output produced by a continuous wavelet transform of the signal for each of a plurality of base functions and for each of a plurality of scales. The method also includes selecting a particular base function from the plurality of base functions, such that the particular base function corresponds to a maximum wavelet coefficient. The method further includes generating a graph plotting a parameterization of each wavelet coefficient output by a continuous wavelet transform of the signal for the particular base function and a corresponding scale. The method may select a particular set of scales from the plurality of scales, such that the particular set of scales correspond to a set of peaks in the graph. And finally, the method may profile the signal as a set of wavelet coefficients corresponding to an output of a wavelet transform utilizing the particular base function and the particular set of scales.

In another embodiment of the present invention, a method for detecting a signal-producing entity is provided. Within this embodiment, the method includes receiving a signal and performing a continuous wavelet transform on the signal utilizing a pre-selected base function and a pre-selected set of scales. The wavelet transform outputs a set of wavelet coefficients, such that the particular wavelet transform profiles a particular signal-producing entity. The method also includes determining a presence of the particular signal-producing entity as a function of wavelet coefficients in the set of wavelet coefficients exceeding a threshold.

In yet another embodiment of the present invention, a signal assessment apparatus is provided. The signal assessment apparatus includes a receiver configured to receive a signal and a processor coupled to the receiver, such that the processor is configured to perform at least one wavelet transform on signals received by the receiver. A database is coupled to the processor and configured to store at least one wavelet transform profile, such that each of the at least one profiles corresponds to a particular signal-producing entity, and such that each of the at least one profiles include a unique combination of a base function and a set of scales.

These and other features, advantages and embodiments will be appreciated by a review of the following detailed description and related drawings.

DETAILED DESCRIPTION OF THE EMBODIMENTS

Figure 1:
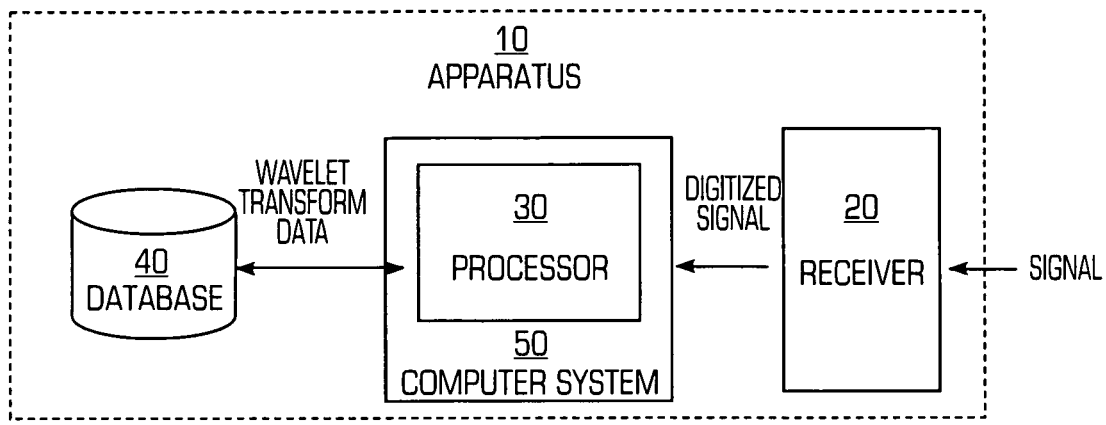
FIG. 1 is a block diagram of an embodiment of the present invention.

The present invention will now be described in detail with reference to the drawings, which are provided as illustrative examples of the invention so as to enable those skilled in the art to practice the invention. Notably, the figures and examples below are not meant to limit the scope of the present invention. Moreover, where certain elements of the present invention can be partially or fully implemented using known components, only those portions of such known components that are necessary for an understanding of the present invention will be described, and detailed descriptions of other portions of such known components will be omitted so as not to obscure the invention. Preferred embodiments of the present invention are illustrated in the Figures, like numerals being used to refer to like and corresponding parts of various drawings.

The embodiments of the invention disclosed herein are directed toward efficiently identifying the source of a signal produced by an animal utilizing wavelet transforms. A wavelet is a waveform of effectively limited duration that has an average value of zero. As will be appreciated by one of ordinary skill in the art, a wavelet transform of a signal is a correlation between the signal and the wavelet base function evaluated at scale 'a' and time 't'. As will be appreciated by one of ordinary skill in the art, there are several different families of base functions and a relatively small number variations within each family. Part of this methodology is a process of choosing which base function works best for the signal feature whose detection and classification we wish to pursue. Wavelet coefficients are the results of the wavelet transform at particular values. Wavelet scales are scaling factors that determine the size of a base function to use in comparison with the signal being examined. The inventor has discovered that wavelet transforms provide an efficient tool for identifying a source of an audio signal produced by an animal. For example, wavelet transforms allow for a specific focus to be made on acoustics having a signature associated with a particular animal species. Also, because wavelet transforms degrade gracefully in the presence of noise, a system may be developed that better tolerates the presence of noise within range of the receiving equipment. Furthermore, wavelet transforms do not take as much processing power to implement as the more common Fourier transforms, which results in a more cost effective solution.

As a preliminary matter, it should be appreciated that some understanding of the target signals must exist. If, for example, one sought to identify a particular species of whale via passive acoustics alone, methods exist for validating that a particular sound belongs to a particular species. Likewise, if one sought to identify a particular species of bird or insect by sound alone, methods exist for validating that a particular sound belongs to a particular species.

In a preferred embodiment, given that examples exist of signals that may be positively identified as belonging to particular sources, an analysis is made of the signals' behavior in wavelet space. In one embodiment, a series of transforms is performed with available base functions, and the results of these transforms are graphed. Such a graph may, for example, plot the maximum value of the wavelet coefficients versus the base function and scale used for each sound. For those sounds where wavelets have good performance, the shape of this graph is then deemed diagnostic for a particular sound. That is, it can be used to reject all other sounds not having this feature. Since the feature has previously been associated with a particular source with a high degree of confidence, a low incidence of false positives is expected.

With this knowledge in mind a filter may be designed that provides a balance between computing power available and the desired accuracy of the filter. Namely, when the features identified in the previous analysis are present, it can be presumed that the source of the feature sought after is within detection range of the equipment being used, and normal triangulation methodologies can be employed to locate it.

In FIG. 1, a block diagram of a signal assessment apparatus according to an embodiment of the invention is provided. As illustrated, apparatus 10 preferably includes a receiver 20, a processor 30, and a database 40.

In a preferred embodiment, receiver 20 is configured to receive a signal. Here, although the description that follows discusses a particular embodiment where receiver 20 is configured to receive bio-acoustical signals, one of ordinary skill in the art would appreciate that receiver 20 could be any of a plurality of signal-receiving apparatuses configured to receive any of a plurality of signals. For example, receiver 20 may be a microphone (for receiving signals via the air), a hydrophone (for receiving signals via the water), or a seismometer (for receiving signals via the ground).

Processor 30 may form part of a computer system 50. Computer system 50 may be any conventional computer system, and may include (or be coupled to) one or more conventional input devices (e.g., a modem, network interface card, wireless (WiFi) receiver, etc.) configured to receive data such as, waveform data, functions, algorithms, parameters and the like, which may be stored in the database and used to perform the inventive method. Computer system 50 may also include other input devices (e.g., a keyboard, mouse, touchpad, touch screen, etc.) to receive user input, commands and other information that can be used to operate the apparatus 10. The computer system 50 and/or processor 30 may also include (or be coupled to) random access memory (RAM), read only memory (ROM), and persistent storage. The processor 30 may use RAM, for example, to temporarily store data, programs, commands and results. The processor 30 may use ROM, for example, for storing firmware, BIOS and/or other like information/instructions. The processor 30 may use persistent storage, for example, to store data, results, software, and the like. The computer system 50 may also include one or more output devices (e.g., a conventional display device, printer, transmitter, etc.) that can be used to provide and transmit the resulting data to a user.

In one embodiment, processor 30 is operatively disposed within computer system 50 and is communicatively coupled to receiver 20 and to database 40 as shown. Processor 30 is configured to perform continuous wavelet transforms on signals received by the receiver 20, and database 40 is configured to store wavelet transform profiles. Preferably, each of the wavelet transform profiles corresponds to a particular signal-producing entity, for example, each of the profiles may be characterized by a unique base function and scale set pairing.

It should be noted that apparatus 10 may be further configured into any of a plurality of embodiments. For example, processor 30 may be configured to profile a signal from a known source as a function of outputs obtained from performing continuous wavelet transforms on the signal. Within such an embodiment, processor 30 may be configured to identify which base function of the plurality of wavelet transforms yields the highest wavelet coefficient for the signal received. Processor 30 may then be further configured to ascertain a scale set corresponding to peaks in the parameterized outputs of a continuous wavelet transform of the signal, wherein the identified base function is utilized. And finally, processor 30 is configured so that the ascertained scale set, along with the identified base function, are stored in database 40 and identified as a wavelet transform profile for the known source.

Figure 2:
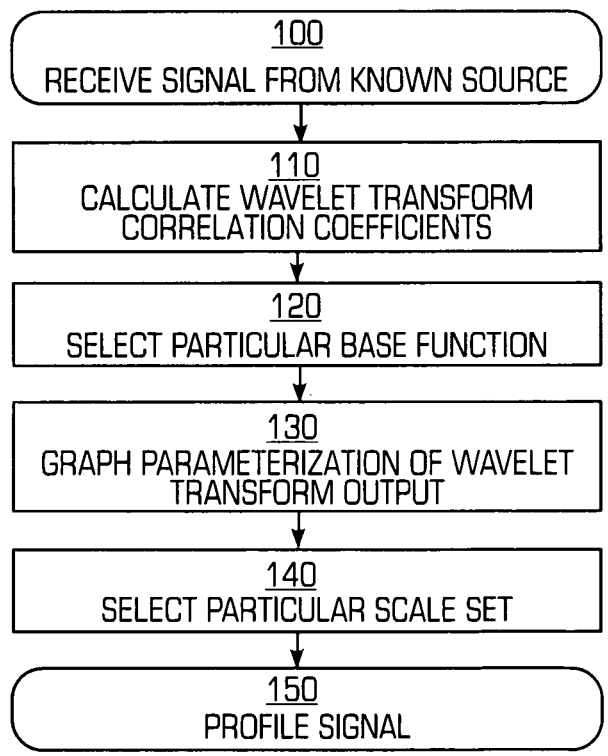
FIG. 2 is a flow chart illustrating a method for profiling a signal according to an embodiment of the present invention.
Figure 3:
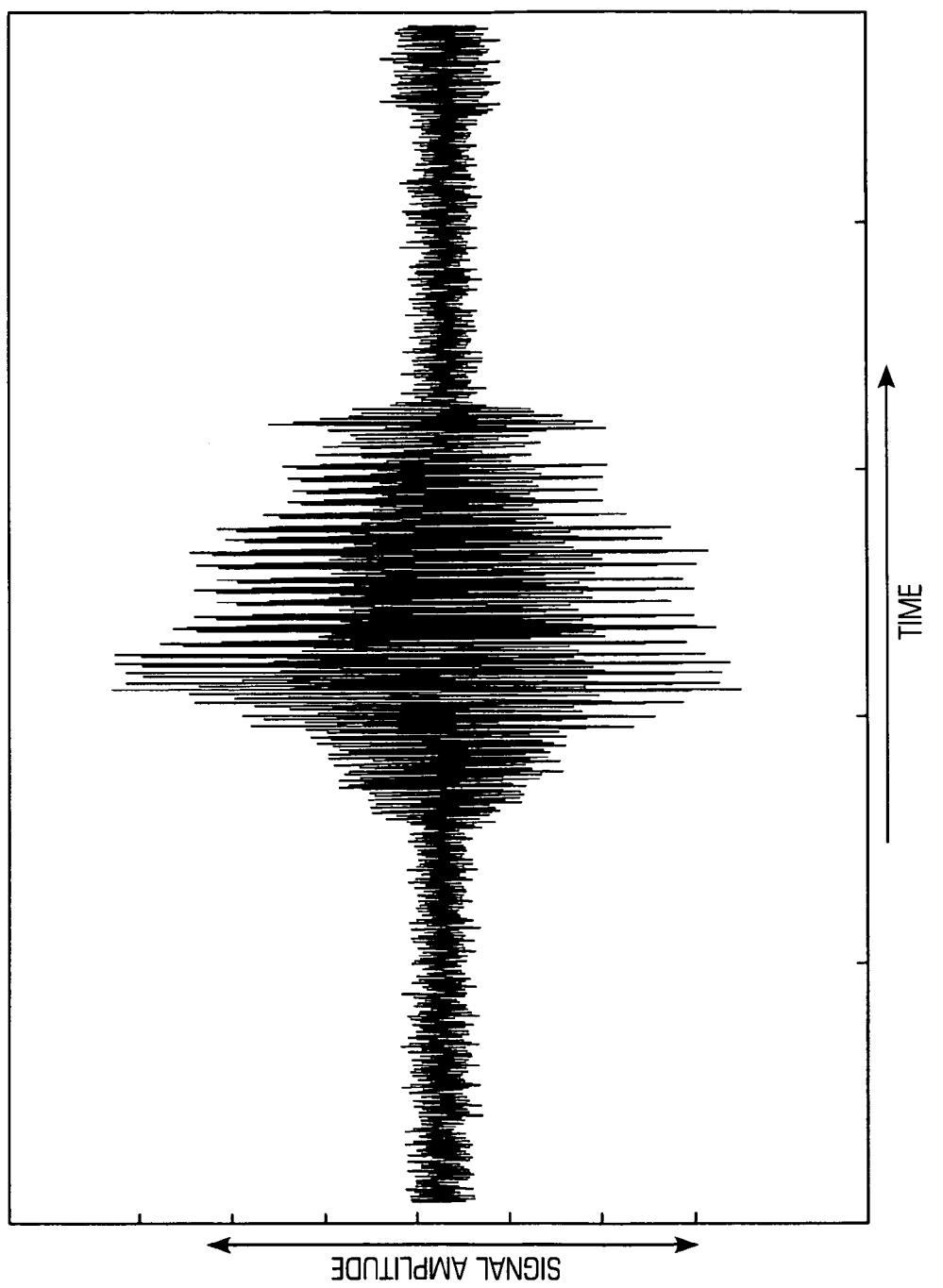
FIG. 3 is a graph of an exemplary amplitude waveform utilized by an embodiment of the present invention.

In FIG. 2, a flow chart illustrating a method for profiling a signal according to an embodiment of the present invention is provided. As illustrated, the method begins at step 100 where a signal produced by a known source is received. One example of a received signal is shown in FIG. 3, which depicts a graph of an exemplary amplitude waveform utilized by an embodiment of the present invention. One of ordinary skill in the art will appreciate that an amplitude waveform is a series of measures of the amplitude of the signal versus time, where that amplitude is proportional to the pressure of the medium through which the signal is conveyed.

In step 110, the method creates a matrix for a plurality of wavelet coefficients. Namely, a matrix is created such that each of the wavelet coefficients correspond to an output produced by a continuous wavelet transform of the signal for each of a plurality of base functions and for each of a plurality of scales.

Figure 4:
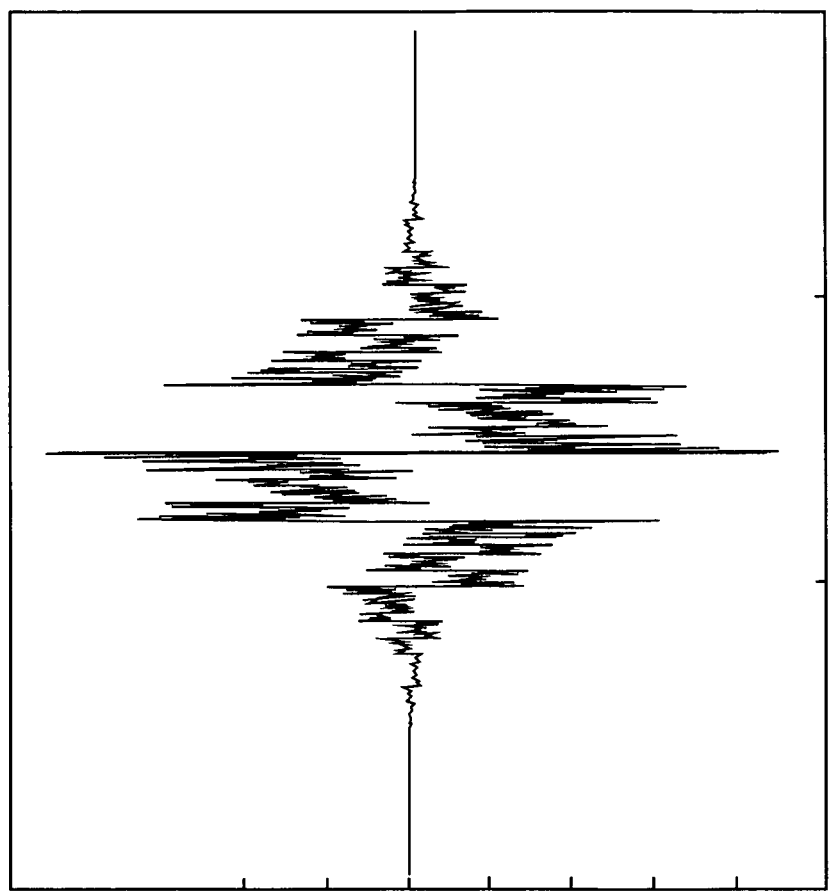
FIG. 4 is a graph of an exemplary base function utilized by an embodiment of the present invention.

The method continues at step 120 where a particular base function from the plurality of base functions is selected. In one embodiment, the particular base function corresponds to a maximum wavelet coefficient. In FIG. 4, a graph of an exemplary base function utilized by an embodiment of the present invention is provided.

Figure 5:
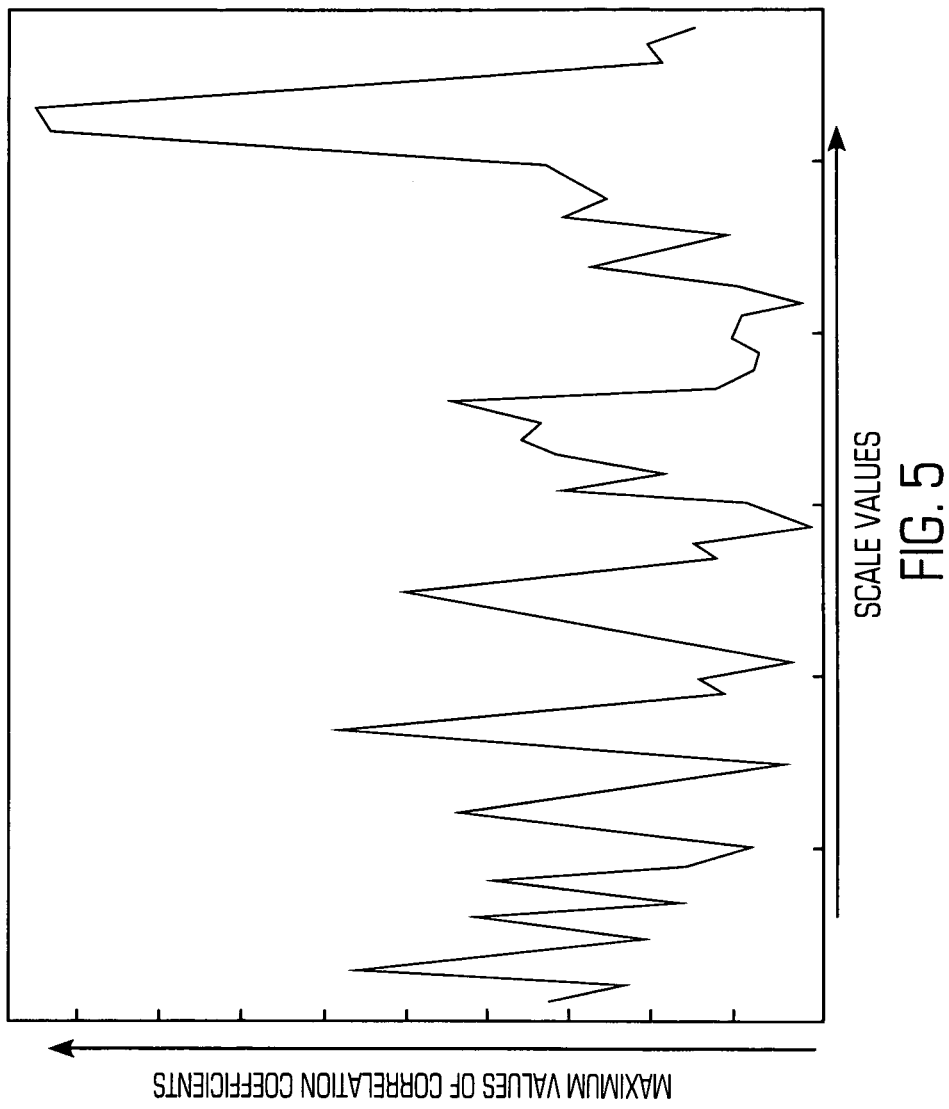
FIG. 5 is a graph of an exemplary parameterization utilized by an embodiment of the present invention.

A graph is then generated at step 130 which plots a parameterization of the wavelet transform output for the particular base function selected in step 120. Particularly, a parameterization of each wavelet coefficient output by a continuous wavelet transform of the signal for the particular base function is plotted versus a corresponding scale. The parameterization may include parameterizing the wavelet coefficients according to average value, mean value, maximum value, variance, standard deviation, or other useful measure. In FIG. 5, a graph of an exemplary parameterization utilized by an embodiment of the present invention is provided, where the parameterization is based on maximum values for the wavelet coefficients.

Figure 6:
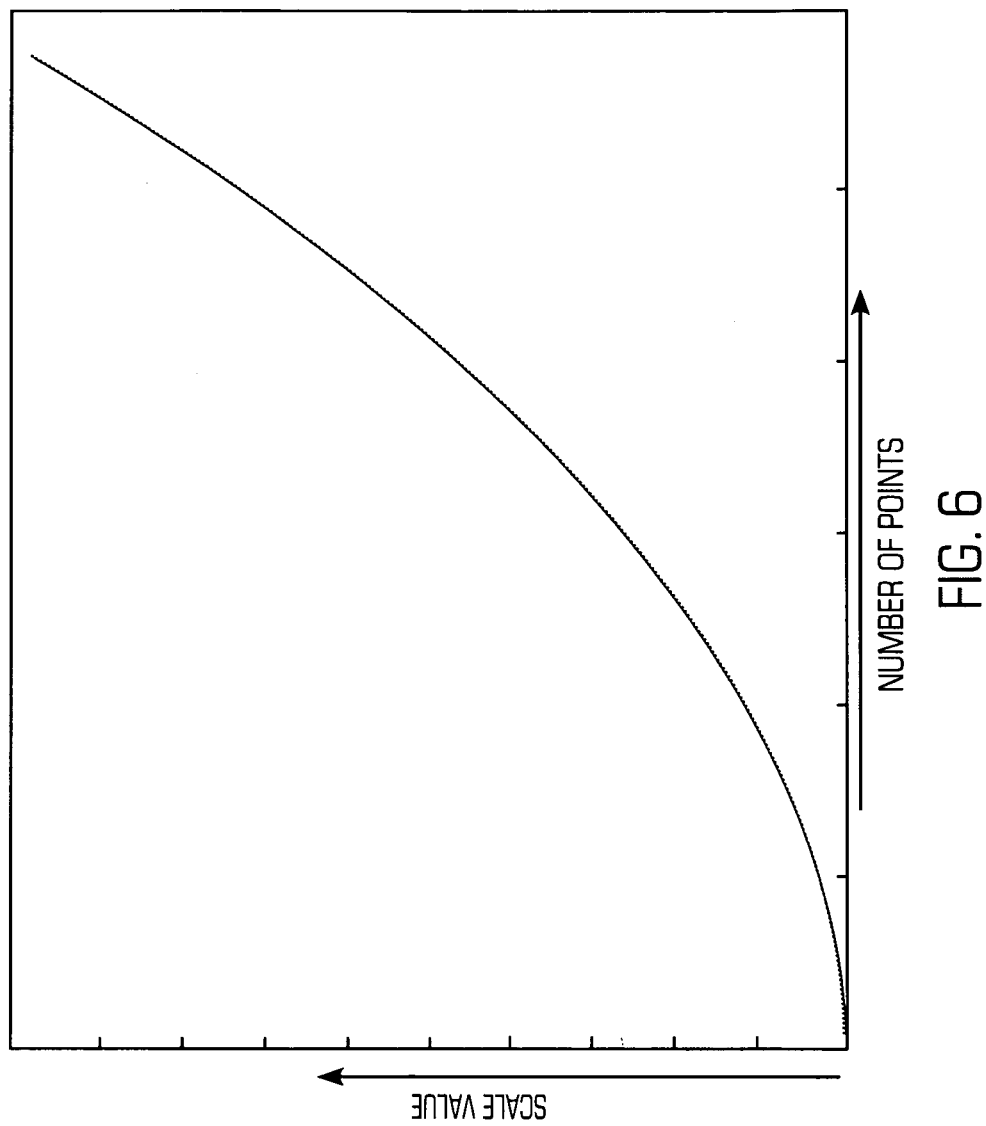
FIG. 6 is a graph of an exemplary scale set utilized by an embodiment of the present invention.

From the graph generated in step 130, a particular set of scales may be used to profile the known source may then be selected at step 140. Here, it should be appreciated that the selected scale set preferably corresponds to a set of peaks in the graph generated in step 130. It should be further appreciated that the selected scale set may correspond to either all the peaks in the graph or a subset of peaks, wherein the subset of peaks selected may vary depending on the particular parameterization. Moreover, due to the nature of wavelet space, the algorithm may be designed to include either all or a subset of the peaks, depending on the confidence levels desired for detection, the processing power available, and the bandwidth of the input signal. FIG. 6 depicts a graph of an exemplary scale set utilized by an embodiment of the present invention.

At this point, the algorithm may be modified to perform the wavelet transform near those peaks alone, for they define the scales at which the maximum values for this transform may be found when it is applied to this waveform. This dramatically reduces the time it takes to compute the transform, allowing such a filter to be implemented in real-time, for example, with commodity hardware. Specifically, the known signal is profiled at step 150 according to a wavelet transform that utilizes the base function selected at step 120 and the scale set selected at step 140. The known signal is profiled as a set of wavelet coefficients corresponding to an output of a wavelet transform utilizing the selected base function and the selected scale set.

Figure 7:
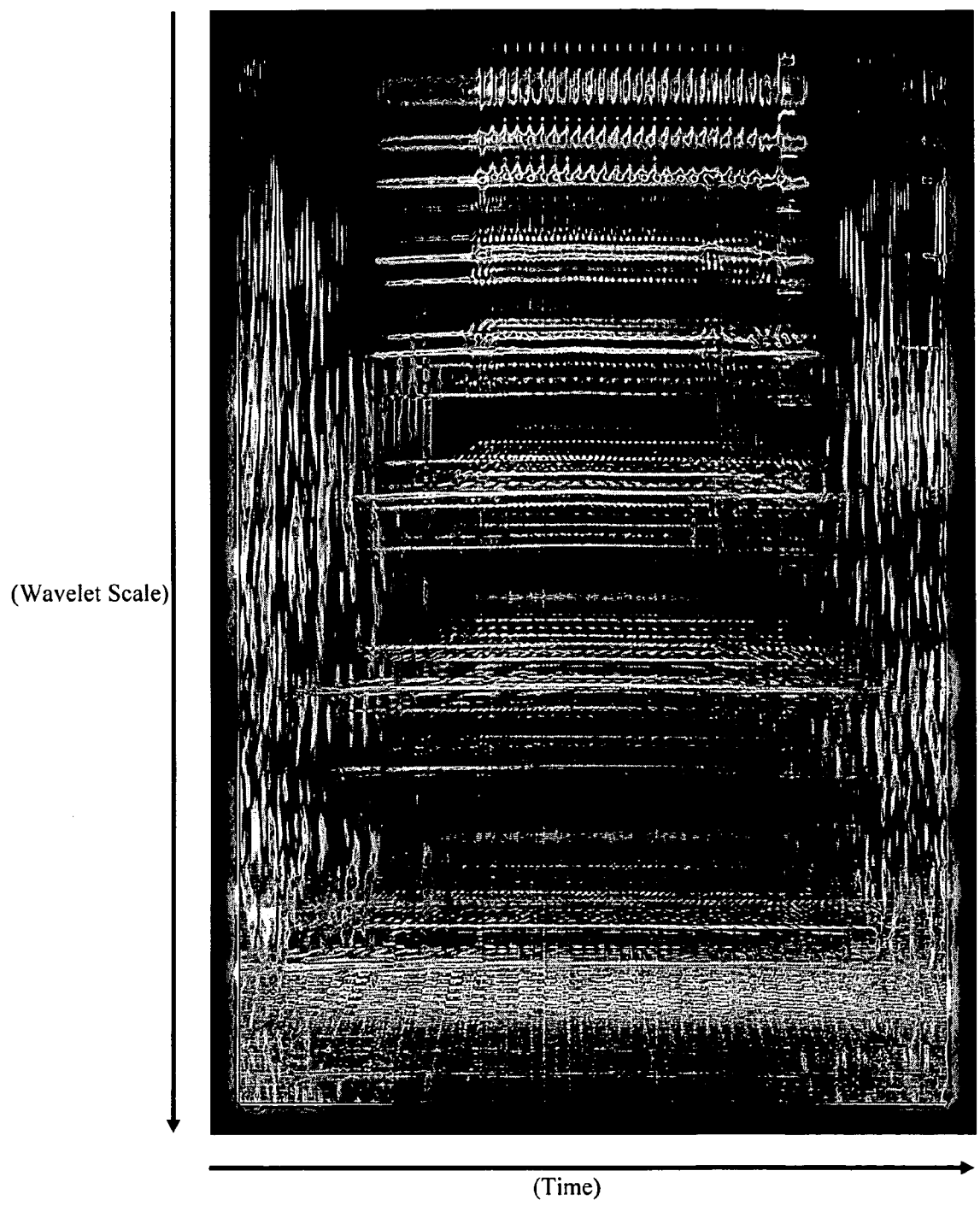
FIG. 7 is an exemplary image of a wavelet transform output according to an embodiment of the present invention.

FIG. 7 illustrates an exemplary image of a wavelet transform output using a particular base function and a particular scale set. Specifically, this is an image created by performing a wavelet transform on a recording of the "A" call of a Blue whale in the eastern north Pacific (that is, off the California coast). As shown, "Time" is on the horizontal axis, increasing from left to right, wherein approximately forty seconds is depicted. The "Wavelet Scale" is shown on the vertical axis, wherein the Wavelet Scale begins at a value of 1 at the top, and increases as you move down the figure to its maximum value. Here, it should be noted that this graphing convention was employed because Wavelet Scale is inversely proportional to the frequency of the signal, whereas the standard convention in spectral analysis is to see higher frequencies at the top of an image. In this particular figure, the brighter regions of the image correspond directly to the maximum value peaks (for example, those peaks shown in FIG. 5).

In one embodiment, the profile may further include an output threshold for each of the wavelet coefficients. In such an embodiment, the output threshold may be tuned by a user and/or set at a default setting. It should also be noted that either a unique or common output threshold may be assigned to each wavelet coefficient.

In other embodiments, apparatus 10 may be configured to detect the presence of a signal-producing entity in a signal having an unknown source. Within this embodiment, processor 30 is configured to detect the entity producing the signal by performing a wavelet transform on the signal, where the wavelet transform has a profile corresponding to a particular signal-producing entity. In a preferred embodiment, each of the profiles in database 40 include an output threshold assigned to each scale of the scale set, such that the presence of the particular signal-producing entity is detected whenever each of the wavelet transform outputs exceed the corresponding output threshold assigned to each scale. In other embodiments, the processor 30 may be configured to tune the output threshold assigned to each scale, either individually or uniformly. In other embodiments, it should also be noted that apparatus 10 may further include a triangulation apparatus configured to approximate a location for the particular signal-producing entity upon detecting its presence.

Figure 8:
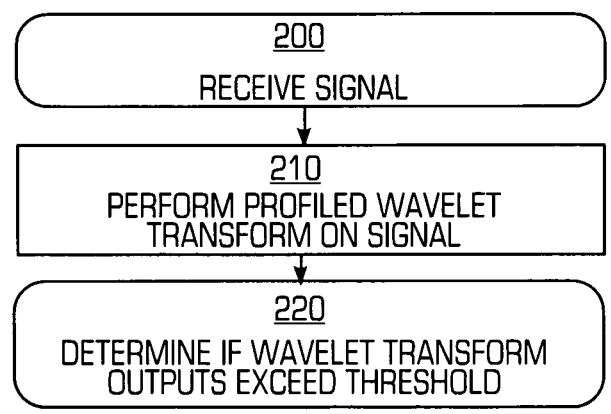
FIG. 8 is a flow chart illustrating a method for detecting a particular signal according to an embodiment of the present invention.

FIG. 8 illustrates a flow chart of a method for detecting a particular signal according to an embodiment of the present invention. As illustrated, the method begins at step 200 where a signal to be analyzed is received. In one embodiment, the signal received is a digitized signal that may either be a recorded signal or a live signal.

A wavelet transform is then performed on the signal at step 210. The transform may either be performed in real-time (for live signals) or run-time (for recorded signals). Here, the wavelet transform used is preferably a transform having a profile as previously described and specific to a particular signal-producing entity. Step 210 may include selecting the particular profile to be used from a plurality of wavelet transforms according to the particular signal-producing entity that is sought to be detected.

Once the wavelet transform has been performed at step 210, the presence of the particular signal-producing entity is then determined at step 220 according to whether the wavelet coefficients exceed or match one or more predetermined threshold values. The wavelet transform profile is used to filter the signal for wavelet coefficients matching the profile, where the transform utilizes a pre-selected base function and a pre-selected set of scales. As stated previously, the profile would preferably include an output threshold for each of the wavelet coefficients. Step 220 may further include tuning the output threshold, in order to assign either a unique or common output threshold to each set of scales. If the wavelet coefficients exceed or match the one or more predetermined threshold values, then the signal is determined to originate from the particular signal-producing entity. If the signal is determined not to originate from the particular signal-producing entity, steps 200-220 may be repeated using profiles from other signal-producing entities until a match is found.

It should be recognized that a number of variations of the above-identified embodiments will be obvious to one of ordinary skill in the art in view of the foregoing description. Accordingly, the invention is not to be limited by those specific embodiments and methods of the present invention shown and described herein. Rather, the scope of the invention is to be defined by the following claims and their equivalents.

What is claimed is:

1. A method for detecting a signal-producing entity, comprising:

receiving an acoustic signal;

performing a wavelet transform on the acoustic signal utilizing a pre-selected base function and a pre-selected set of scales to generate a set of wavelet coefficients and wherein the particular wavelet transform profiles a particular signal-producing animal; and determining a presence of the particular signal-producing animal when the set of wavelet coefficients exceed a threshold.

2. The method of claim 1, wherein the wavelet transform is selected from a plurality of wavelet transforms, each of the plurality of wavelet transforms corresponding to a different signal-producing animal, and wherein each of the plurality of wavelet transforms utilizes a unique combination of a pre-selected base function and a pre-selected set of scales.

3. The method of claim 1, wherein the threshold comprises a tunable threshold.

4. The method of claim 1, wherein each of the wavelet coefficients is assigned a unique threshold, and wherein the determining step comprises determining whether each of the wavelet coefficients exceeds its corresponding unique threshold.

5. The method of claim 1, wherein the receiving step comprises receiving a recorded acoustic signal, and wherein the performing step comprises performing the transform in run-time.

6. The method of claim 1, wherein the performing step is performed in real-time.

7. The method of claim 6 further comprising the step of triangulating a location for the particular signal-producing animal.

8. The method of claim 2 further comprising storing the plurality of wavelet transforms in a database.

9. A signal assessment apparatus, comprising:
a receiver configured to receive an acoustic signal;
a database configured to store at least one wavelet transform profile, wherein each of the at least one profiles identifies a particular signal-producing animal and includes a set of wavelet coefficients corresponding to an output of a wavelet transform using a unique combination of a base function and a set of scales;
a processor coupled to the receiver and the database, wherein the processor is configured to perform at least one wavelet transform on the acoustic signal received by the receiver based on the at least one wavelet transform profile in the database having the base function and the set of scales to generate a set of wavelet coefficients; and
wherein the processor detects a presence of the particular signal-producing animal by comparing the generated set of wavelet coefficients and the set of wavelet coefficients of the at least one wavelet transform profile.

10. A signal assessment apparatus according to claim 9 further comprising a triangulation apparatus.

11. A signal assessment apparatus according to claim 9, wherein the processor is configured to perform only one particular wavelet transform, and wherein the one particular wavelet transform corresponds to a particular wavelet transform profile stored in the database.

12. A signal assessment apparatus according to claim 11, wherein the at least one profile includes an output threshold assigned to each scale, and wherein the processor is configured to detect the particular signal-producing animal when each of a set of particular wavelet transform outputs exceed the corresponding output threshold assigned to each scale.

13. A signal assessment apparatus according to claim 12, wherein the processor is configured to tune the output threshold assigned to each scale.

14. A signal assessment apparatus according to claim 9, wherein the processor is configured to ascertain the at least one wavelet transform profile as a function of outputs obtained from performing a plurality of wavelet transforms on the signal.

\* \* \* \* \*